United States Patent [19]

Melnik et al.

[11] Patent Number: 5,082,661

[45] Date of Patent: Jan. 21, 1992

[54] ODORLESS COSMETIC COMPOSITIONS IN GELATIN CAPSULES

[75] Inventors: Joseph Melnik, Milford; Michael C. Cheney, Fairfield, both of Conn.; Anthony Vargas, Mahwah, N.J.

[73] Assignee: Elizabeth Arden Co., Division of Conopco, Inc., New York, N.Y.

[21] Appl. No.: 588,250

[22] Filed: Sep. 26, 1990

[51] Int. Cl.$^5$ .................. A61K 7/021; A61K 9/64
[52] U.S. Cl. .................. 424/401; 424/408; 424/400; 424/451; 424/456; 424/59; 424/70; 514/962; 514/725; 514/801; 514/784; 514/828; 514/844; 514/859; 514/852; 514/970; 514/974; 514/873; 514/922
[58] Field of Search .............. 424/401, 451, 455, 456, 424/408; 514/847, 725, 784, 785, 962, 852, 815, 974, 970

[56] References Cited

U.S. PATENT DOCUMENTS

| | | | |
|---|---|---|---|
| 2,686,751 | 8/1954 | Embree et al. | 514/785 |
| 4,246,257 | 1/1981 | Elliott et al. | 424/78 |
| 4,370,319 | 1/1983 | Chapin et al. | 424/184 |
| 4,515,784 | 5/1985 | Bogardus et al. | 514/63 |
| 4,724,240 | 2/1988 | Abrutyn | 514/847 |
| 4,826,828 | 5/1989 | Wilmott et al. | 514/725 |
| 4,888,363 | 12/1989 | Dulak et al. | 514/725 |
| 4,950,688 | 8/1990 | Bowser et al. | 514/847 |

FOREIGN PATENT DOCUMENTS 2632936 12/1989 France.
59-186910 10/1984 Japan.

Primary Examiner—Thurman K. Page
Assistant Examiner—D. Colucci
Attorney, Agent, or Firm—Milton L. Honig

[57] ABSTRACT

A cosmetic product is disclosed in the form of a gelatin walled capsule encompassing a cosmetic composition that includes a carrier which is a silicone polymer and an antioxidant. The antioxidant operates to inhibit degradation of the gelatin wall to prevent malodors from being generated. Retinoic acid derivatives such as retinyl palmitate are especially effective as antioxidants.

13 Claims, No Drawings

ODORLESS COSMETIC COMPOSITIONS IN GELATIN CAPSULES

BACKGROUND OF THE INVENTION

1. Field of the Invention

The invention relates to odorless cosmetic compositions within gelatin capsules.

2. The Related Art

Traditionally, cosmetic products have been packaged in containers sufficiently large to provide multiple doses. More recently, there has been a trend towards single or unit dose packages. Capsules, especially those formed from gelatin, are the newest vehicles for delivering single dose cosmetic products. For instance, the Revlon Corporation has introduced a product called Age-less ® which is a formula comprising vitamin E, sunscreens and moisturizers sealed into vitamin-like capsules.

La Prairie Corporation has introduced a product called Skin Caviar ® which is a skin-care lotion contained in tiny egglike globes that are popped and rubbed onto the face. French Patent 2,632,936 (Dana) reports enclosing small quantities of perfume or other liquid cosmetics in spherical capsules formed from thin gelatin walls or inert plastic. The capsules measure in size between 2 and 4 mm.

Based upon cost considerations and long experience with pharmaceuticals, gelatin has become the wall material of choice in capsule technology. More particularly the soft gelatin variety, because of its elastic nature, has been of most interest to cosmetic packagers. However, an unexpected problem has been encountered in developing liquid cosmetics held within gelatin capsules. The problem is one of malodor apparently generated by the interaction of liquid cosmetic with the gelatin wall. The odor has been described as an amine smell, possibly arising from proteinaceous constituents of the gelatin wall. Malodor represents a significant problem to cosmetic products, especially products which are formulated without perfume.

Accordingly, it is an object of the present invention to provide a gelatin capsule containing a unit dose of cosmetic product which is acceptable to consumers.

A further object of the present invention is to provide a gelatin capsule containing a unit dose of cosmetic product that is malodor-free, especially a product without perfume.

A still further object of the present invention is to provide a gelatin capsule containing a unit dose of cosmetic product that can be stored for long periods of time without the cosmetic adversely interacting with the gelatin.

These and other objects of the present invention will become more readily apparent upon consideration of the more detailed description of the invention that follows.

SUMMARY OF THE INVENTION

A cosmetic product is provided comprising:
a capsule having walls formed of a gelatin; and
a cosmetic composition pharmaceutically acceptable to a human body, the composition comprising:
(i) from about 5 to about 99% by weight of a pharmaceutically acceptable carrier compatible with the gelatin walls which is a silicone polymer; and
(ii) an antioxidant present in an effective amount to inhibit degradation of the gelatin walls.

Advantageously, the cosmetic composition is a non-aqueous system. Most preferred of the antioxidants are derivatives of retinoic acid (vitamin A) including esters such as retinyl palmitate.

DETAILED DESCRIPTION

Now it has been discovered that antioxidants can be utilized to reduce and even eliminate detected odors arising from gelatin walls of cosmetic product capsules. Although not wishing to be bound by any theory, it is suggested that odor arises from breakdown of proteinaceous material of the gelatin wall and that the antioxidant operates to inhibit this breakdown.

A variety of antioxidants may be suitable for purposes of the present invention. These include hindered phenols, retinoic acid, tocopherol, erythorbic acid, citric acid, anthranilic acid and derivatives of the foregoing materials.

Among the hindered phenols may be included 2,6-di-tert-butyl para-cresol (also known as butylated hydroxy toluene); butylated hydroxy anisole (available from UOP); propyl gallate (available from Inolex Corporation); 2,2'-methylene bis(4-ethyl-6-tert-butylphenol) (sold as Cyanox 2246 by American Cyanamid Corporation); 2,5-di-tert-butylhydroquinone, hydroquinone monomethyl ether and mono-tert-butylhydroquinone (all available from Eastman Chemical Company); tris(3,5-di-t-butyl-4-hydroxybenzyl)isocyanurate and 3,5-di-tert-butyl-4-hydroxyhydrocinnamic acid triester with 1,3,5-tris(2-hydroxyethyl)-s-triazine-2,4,6(1H,3H,5H)-trione (both available from B.F. Goodrich Company); and tetrakis(methylene 3-(3',5'-di-tert-butyl-4'-hydroxyphenyl proprionate) methane (sold as Irganox 1010 by Ciba-Geigy). Alpha tocopherol (vitamin E) as well as fatty esters thereof such as tocopheryl, linoleate and palmitate may be useful antioxidants. Citric acid may be suitable as well as fatty esters thereof. Erythorbic acid and salts, such as sodium erythorbate can be employed as a antioxidant. Most effective, however, are derivatives of retinoic acid which may include retinol, retinoic acid and fatty acid esters thereof, such as retinyl palmitate, retinyl laurate and retinyl oleate.

Amounts of the antioxidant may range anywhere from about 0.001 to about 5%, preferably from about 0.1 to about 1%, optimally from about 0.3 to about 0.8% by weight of the total cosmetic composition.

An important further component of the compositions of this invention is a pharmaceutically acceptable carrier compatible with the gelatin walls of the capsule. A wide variety of silicone polymers may be useful as the carrier. Particularly advantageous are the polyalkyl siloxanes and the polyalkyl phenyl siloxanes. Silicones for this invention may be those with viscosities ranging anywhere from about 0.5 to 10,000,000 centistokes at 25° C. Mixtures of low and high viscosity silicones may be incorporated into the cosmetic formulations. High viscosity non-volatile polyalkyl siloxanes usually range in viscosity from about 10 up to about 10,000,000 centistokes. Polydimethyl siloxanes of high viscosity are available commercially under the trademarks SE 30 Gum from the Dow Corning Company and as Vicasil from the General Electric Company. Low viscosity or volatile polydimethyl siloxanes are available as cyclomethicone in pentamer and/or tetramer form, often present at 9:1 blends. Viscosities of the volatile silicones may range from about 0.5 to less than 10 centistokes at 25° C.

For purposes of this invention, mixtures of high and low viscosity polydimethyl siloxanes may be employed, one such example being Dow Corning X2-1146A Fluid. Amounts of silicone which can be utilized in the compositions of this invention range anywhere from about 5 to about 99%, preferably from about 25 to about 90% by weight of the composition.

Emollients are often incorporated into cosmetic compositions of the present invention. Levels of such emollients may range from about 0.5 to about 50%, preferably between about 5 and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl erucate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5 to 10% by weight of the composition. Exemplary thickeners are cross-linked polyacrylate materials available under the trademark Carbopol from the B.F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Various types of active ingredients may be present in cosmetic compositions of the present invention. Actives are defined as skin or hair benefit agents other than emollients and other than ingredients that merely improve the physical characteristics of the composition. Although not limited to this category, general examples include sunscreens, tanning agents, skin anti-wrinkling agents, anti-dandruff agents, anti-acne agents and hair growth stimulants.

Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Anti-wrinkling agents are best exemplified by the 2-hydroxyalkanoic acids, prostaglandins, retinoic acids, ceramides and their derivatives. These agents may be present anywhere from about 0.00001 to about 5%, preferably from about 0.0001 to about 1%, optimally between about 0.01 and 0.2% by weight of the total composition. Most preferred of the active compounds mentioned above is 2-hydroxyoctanoic acid, retinol and pigskin or bovine-brain lipid ceramides. Further identification of ceramide structures may be found in U.S. Pat. No. 4,950,688 (Bowser et al), herein incorporated by reference.

Other adjunct minor components may also be included in the cosmetic compositions. These ingredients may include preservatives, coloring agents, opacifiers and perfumes. Amounts of these materials may range anywhere from 0.001 up to 20% of the composition.

Capsules of the present invention are formed from gelatin walls. These walls may either be soft or hard. Preferably, however, the walls are elastic or soft. Gelatin for soft capsules normally will be selected from low-bloom Type A (170–180 g), Type B (150–172 g), or a mixture of Types A and B. The manufacturing process for preparing such capsules can utilize a rotary die fed from two plasticized gelatin sheets which form a sealed chamber or compartment around the material being encapsulated. The size of the capsules may range from No. 0 to 2. Overall length of the capsules will normally range from about 0.5 to about 5 cm, preferably 1 to about 3 cm, optimally about 1.5 cm.

Amounts of cosmetic product held within these capsules may range in weight anywhere from about 0.05 to about 5 grams, preferably from about 0.3 to about 2 grams, optimally about 1 gram.

The following examples will more fully illustrate selected embodiments of this invention. All parts, percentages and proportions referred to herein and in the appended claims are by weight unless otherwise indicated.

EXAMPLE I

A gelatin capsule of about 1.5 cm length was formed and a cosmetic composition of the following formula was enclosed therein:

| SKINCARE TREATMENT | |
|---|---|
| Ingredient | Wt. % |
| Silicone Gum SE-30 | 10.00 |
| Silicone Fluid 345 | 20.00 |
| Silicone Fluid 344 | 58.49 |
| Squalene | 10.00 |
| Ceramides | 0.01 |
| Vitamin A Palmitate | 0.50 |
| Vitamin E Linoleate | 0.50 |
| Herbal Oil | 0.50 |

Capsules with the above composition were stored for over three months at room temperature. When the capsules were opened, a panel of evaluators determined that there was no malodor or other smell associated with the composition.

Gelatin capsules with identical composition except for the absence of vitamin A palmitate were also prepared. After a period of one week, the capsules were opened and the panel again assessed odor. This time, the compositions had a very distinct amine odor which was quite unpleasant. From these results, it is evident that the vitamin A palmitate was essential for maintaining the proper odor characteristics of the composition.

EXAMPLE II

Another series of gelatin capsules similar to that of Example I was formed and a cosmetic composition of the following formula was enclosed therein:

| SKINCARE TREATMENT | |
|---|---|
| Ingredient | Wt. % |
| Silicone Gum SE-30 | 10.000 |
| Silicone Fluid 345 | 20.000 |
| Silicone Fluid 344 | 58.490 |
| Squalene | 5.975 |
| Ceramides (Neural Lipid Extract) | 0.010 |
| Wheat Germ Oil | 2.000 |
| Sesame Oil | 0.500 |
| Jojoba Oil | 2.000 |
| Vitamin E Linoleate | 0.500 |
| Herbal Oil | 0.500 |
| Ceramide I Mix | 0.025 |

Capsules with the above composition after a storage period of one week were opened and found to possess a foul odor. A series of deletion experiments were then performed removing each oil (wheat germ, sesame and jojoba), one at a time, then encapsulating and evaluating for odor. Moreover, all oils in question were removed, encapsulated and then evaluated for odor of the fill material.

In all cases at room and elevated (120°) temperatures, it was determined that the same foul odor was present. Thereafter the full formula (with oils) was encapsulated and Vitamin A palmitate at 0.5% was incorporated therein. These samples showed no foul odor at either room or elevated temperatures.

All encapsulation performed in Examples I and II were conducted as follows. The gelatin formulation utilized was a combination of rendered pig gelatin, sorbitol/glycerin mixture for plasticizing and titanium dioxide for color. This mixture was then heated to molten liquid and formed into two sheets which were run across two rotary dies representing each half of the gelatin capsule. The dies were rolled together with the sheets of gelatin pressing one another and fill material was injected into the pressed gelatin cavity. Thereafter the capsules were completely sealed at the top while the rotary dies were spun downward to release a completed capsule with fill material inside. Finished capsules were then washed with NAPTHA to remove excess moisture and tumbled (air-dried) for one hour. Capsules were then laid on trays and air dried for four days at low relative humidity.

The foregoing description and examples illustrate selected embodiments of the present invention and in light thereof variations and modifications will be suggested to one skilled in the art, all of which are within the spirit and purview of this invention.

What is claimed is:

1. A cosmetic product comprising:
   a capsule having walls formed of a gelatin; and
   a cosmetic composition pharmaceutically acceptable to a human body, said composition comprising:
   (i) from about 5 to about 99% by weight of a pharmaceutically acceptable carrier compatible with said gelatin walls which is a silicone polymer; and
   (ii) an antioxidant present in an effective amount to inhibit degradation of said gelatin walls.

2. A product according to claim 1 wherein said cosmetic composition is substantially anhydrous.

3. A product according to claim 1 wherein said silicone polymer is the major component present in an amount of from about 25 to about 90% by weight of said cosmetic composition.

4. A product according to claim 1 wherein said cosmetic composition comprises an active ingredient selected from the group consisting of sunscreens, tanning agents, skin anti-wrinkling agents, anti-dandruff agents, anti-acne agents, hair growth stimulants and mixtures thereof.

5. A product according to claim 1 wherein said antioxidant is selected from the group consisting of hindered phenols, retinoic acid, tocopherol, erythorbic acid, citric acid, anthranilic acid and derivatives thereof including salts and esters.

6. A product according to claim 5 wherein said retinoic acid derivatives are selected from the group consisting of retinol, retinoic acid and fatty esters thereof.

7. A product according to claim 6 wherein said retinoic acid derivative is retinyl palmitate.

8. A product according to claim 1 wherein said antioxidant is present in an amount from about 0.001 to about 5% by weight of the total cosmetic composition.

9. A product according to claim 1 wherein said antioxidant is present in an amount from about 0.3 to about 0.8% by weight of the total cosmetic composition.

10. A product according to claim 1 wherein said silicone polymer is selected from the group consisting of polyalkyl phenyl siloxanes, polyalkyl siloxanes and mixtures thereof.

11. A product according to claim 10 wherein said silicone polymer is polydimethyl siloxane.

12. A product according to claim 1 further comprising from about 0.00001 to about 5% by weight of a ceramide selected from the group consisting of pigskin lipid ceramides, bovine-brain lipid ceramides and mixtures thereof.

13. A product according to claim 1 further comprising from about 0.0001 to about 5% by weight of 2-hydroxyoctanoic acid.

* * * * *